United States Patent [19]

Hymes et al.

[11] 4,306,551
[45] Dec. 22, 1981

[54] STERILE IMPROVED BANDAGE AND SEALANT

[75] Inventors: Alan C. Hymes, Hopkins; Lincoln T. Ong, Minnetonka; Garry R. Persons, Edina, all of Minn.

[73] Assignee: LecTec Corporation, Eden Prairie, Minn.

[21] Appl. No.: 173,154

[22] Filed: Jul. 28, 1980

[51] Int. Cl.³ .............................................. A61L 15/00
[52] U.S. Cl. ..................................... 128/156; 424/26; 106/124; 260/29.1 R; 428/343
[58] Field of Search ........................... 128/155–156, 128/283, 640, 641; 424/26, 28, 31; 106/124, 205, 210, 129, 227; 260/29.1 R; 428/261, 343

[56] References Cited

U.S. PATENT DOCUMENTS

| 3,249,109 | 5/1966 | Maeth et al. | 128/156 |
| 3,475,363 | 10/1969 | Gander | 428/343 |
| 3,612,053 | 10/1971 | Pratt | 128/283 |
| 3,640,741 | 2/1972 | Etes | 128/283 |
| 3,946,730 | 3/1976 | Monter | 128/641 |
| 3,972,995 | 8/1976 | Tsuk et al. | 128/156 |
| 4,253,460 | 3/1981 | Chen et al. | 128/156 |

FOREIGN PATENT DOCUMENTS

| 495110 | 8/1977 | Australia | 128/156 |
| 2919923 | 11/1979 | Fed. Rep. of Germany | 128/156 |

*Primary Examiner*—C. Fred Rosenbaum
*Attorney, Agent, or Firm*—Williamson, Bains, Moore & Hansen

[57] ABSTRACT

A flexible, liquid absorbent, adhesive bandage includes a backing element and a substrate attached to the backing element. The substrate comprises a homogeneous, hydrophilic, stable matrix including a solid phase formed of a synthetic polymer, a long chain polysaccharide, or a combination thereof. The liquid phase of the matrix consists of a hydric alcohol, carbohydrates or proteins.

9 Claims, 4 Drawing Figures

STERILE IMPROVED BANDAGE AND SEALANT

BACKGROUND OF THE INVENTION

The present application relates to a sterile bandage and more particularly to a sterile bandage which has special utility as a surgical dressing and a sealant. The chemical composition and physical characteristics are of principle importance with respect to this novel bandage.

Attempts have been made to develop bandages which are self-adhesive, absorbent and sterile. For example, U.S. Pat. No. 3,339,564, discloses a self-adhesive bandage which is adapted to adhere to a moist surface such as the moist mucosa of the oral cavity. However, one of the essential materials of this self-adhesive bandage is an adhesive gum, preferably polyisobutylene, which is hydrophobic. Similarly, U.S. Pat. Nos. 3,598,122 and 3,598,123, disclose bandages which contain drugs that are continually released from an adhesive layer. These bandages are formed of layered materials which have encapsulated drugs in the adhesive layer. Even though the bandage disclosed in these prior art patents are said to be self-adhesive and are satisfactory vehicles for drugs, it is not believed that these bandages could effectively function as surgical dressings inasmuch as they are not sterile. In this regard, it is pointed out that surgical dressings should not only be capable of adsorbing liquids, but it is an essential requirement that the surgical dressing be sterile. The only practical sterilization technique is by irradiation and it is not believed that the prior art bandages can be irradiated without affecting the adhesive characteristics thereof.

SUMMARY OF THE INVENTION

Therefore, it is a general object of this invention to provide a sterile, self-adhesive novel bandage which readily absorbs liquid exudate from a wound. The bandage is comprised of a flexible backing element and a self-adhesive substrate which becomes increasingly tacky in the presence of moisture and which has a high degree of absorbency for continuously absorbing liquid exudate from a wound while remaining dimensionally stable during such absorption. Sterilization may be accomplished by irradiation without affecting the self-adhesive properties of the substrate.

These and other objects and advantages of this invention will more fully appear from the following description made in connection with the accompanying drawings, wherein like reference characters refer to the same or similar parts throughout the several views.

FIGURES OF THE DRAWINGS

DESCRIPTION OF THE PREFERRED EMBODIMENT OF THE INVENTION

The bandage of the present invention has adhesive properties for maintaining contact with the skin, as well as, possessing a certain amount of elasticity for movement with the skin. The bandage is intended to be easily handled and in all respects is non-irritating to the patient.

Figure 1:
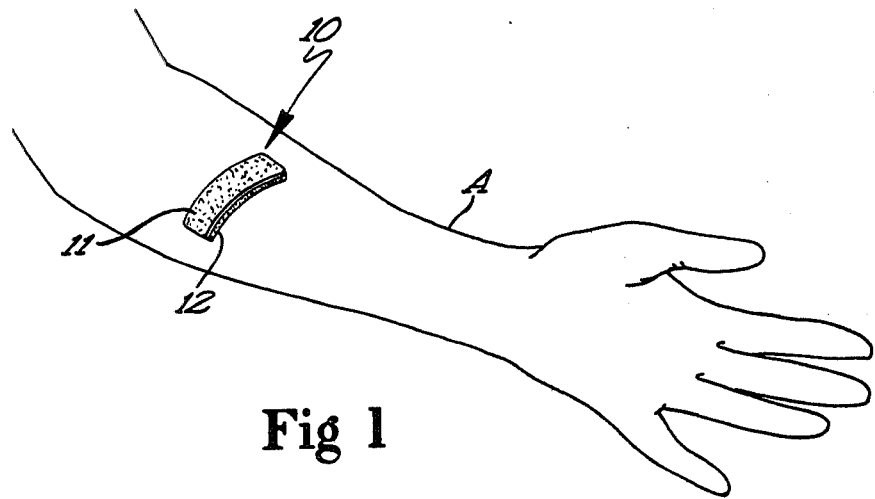
FIG. 1 is a perspective view illustrating the novel bandage applied to the arm of a patient.
Figure 2:
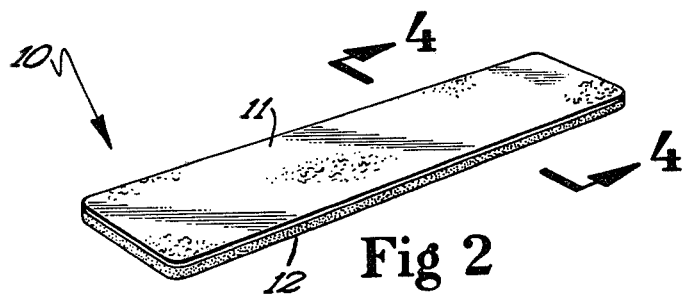
FIG. 2 is a perspective view of a bandage illustrated in FIG. 1.
Figure 3:
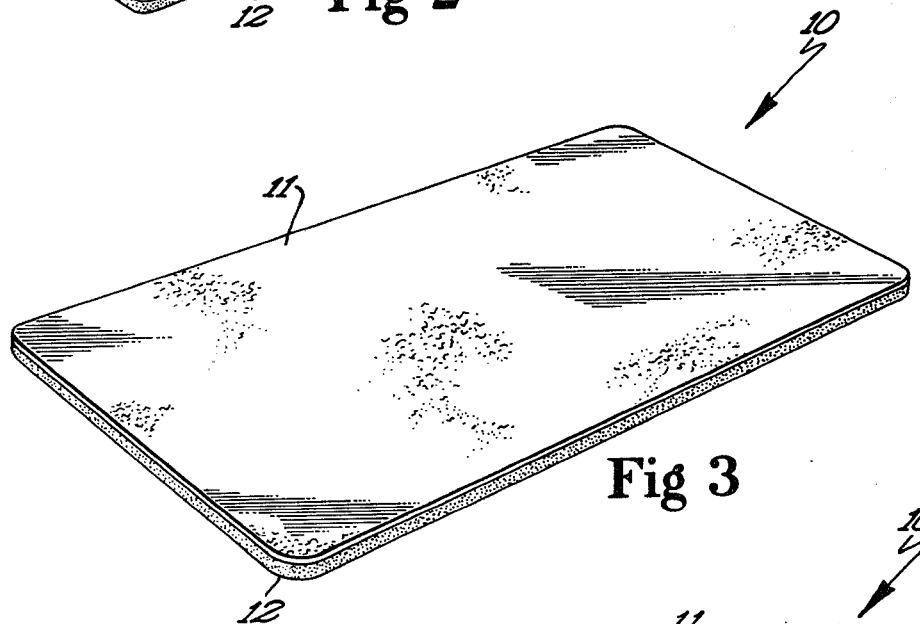
FIG. 3 is a perspective view of the bandage used as a surgical dressing.
Figure 4:
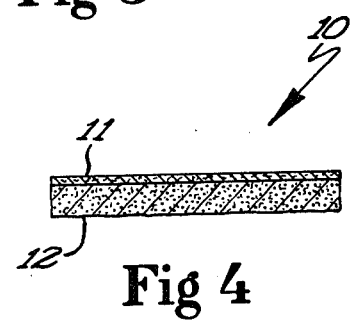
FIG. 4 is a cross-sectional view taken approximately along line 4—4 of FIG. 2 and looking in the direction of the arrows.

Referring now to the drawings, it will be seen that the bandage of the present invention is thereshown. The bandage, designated by the reference numeral 10 includes a backing member 11 and a self-adhesive substrate 12 which is secured to one surface of the backing. The backing element 11 and the substrate 12 are both illustrated as rectangular sheets of material of uniform thickness. It is pointed out that the bandage 10 is intended to be of uniform thickness but may have any other configurations although the rectangular shape is preferred. In use, the bandage is applied with the substrate 12 in direct contact with the skin to cover a non-surgical wound, a surgical wound or burned tissue. In FIG. 3, the embodiment illustrated therein is a surgical dressing and will be applied to the patient to cover a surgical wound.

Primary to the unique structure of the bandage is the hydrophilic adhesive properties of the substrate which enhance the adhesion thereof to the skin. The substrate not only absorbs moisture making it ideal for use as a surgical dressing, but the substrate becomes tackier as it absorbs moisture.

The substrate 12 may be formed from naturally occurring materials such as karaya gum, guar gum, gum acacia, locust bean gum, irradiated karaya (subjected to 2.5 Mrads of gamma irradiation) and sorbitol 70% and other polysaccharides. The substrate may also be formed from synthetic polymers such as carboxymethylcellulose, carboxypropylcellulose, polyacrylic acid, poly-acrylamide and their cogeners. Examples are poly-acrylic acid in molecular weights 250,000, 450,000, 1,000,000, and 4,000,000 and poly-acrylamide sold under the trademark, Reten by the Hercules Co. When monomers such as acrylic acid or acrylamide are polymerized, it is necessry to use activators. Activators, which are used during polymerization, may include ferrous sulfate, sodium metabisulfite, and potassium persulfate.

Solutions or emulsions or saccharides or polysaccharides or proteins may be used in forming the matrix. Alternatively, a combination of a solution or emulsion of polysaccharide, saccharides or proteins may be used in the liquid phase of the matrix.

The substrate 11 which is a stable matrix includes a solid phase comprising a synthetic polymer matrix, a karaya matrix, or a matrix of karaya and synthetic polymer. The solids of the matrix comprise 30% to 50% by weight of the matrix 11.

When karaya or other material gums are used in forming the matrix, it is necessary to use polyacrylic acid and/or polyacrylamide to protect karaya during irradiation. However, a predetermined concentration of salts, such as aluminum sulfate or sodium chloride, may be used in the matrix with karaya in some instances in lieu of polyacrylamide and/or polyacrylic acid. For example, concentrations of approximately 6% sodium chloride or aluminum sulfate may be used with karaya in forming the solid phase of the matrix.

It has also been found that vinyl acetate dioctyl maleate copolymer may also be advantageously used in forming the solid phase of the matrix. Vinyl acetate dioctyl maleate copolymer (sold under the trademark "Flexbond 150" by Air Products and Chemicals, Inc., and sold under the trademark "Bostik 8761" by the Bostik Co., Inc.) will intensify the tackiness of the bandage.

Examples of the substrate for use as a bandage and surgical dressings and sealant are as follows:

EXAMPLE 1

|  | Nominal Amounts of Ingredients | Range of Ingredients |
| --- | --- | --- |
| Polyacrylamide | 5% | 2-20% |
| Karaya | 40% | 10-40% |
| Glycerol | 55% | 50-70% |

EXAMPLE 2

|  |  |  |
| --- | --- | --- |
| Polyacrylic acid | 10% | 2-25% |
| Polyacrylamide | 10% | 2-25% |
| Karaya | 20% | 5-40% |
| Glycerol | 60% | 50-70% |

EXAMPLE 3

|  | Nominal Amounts of Ingredients | Range of Ingredients |
| --- | --- | --- |
| Polyacrylamide | 15% | 2-25% |
| Polyacrylic acid | 15% | 2-25% |
| Glycerol | 70% | 50-70% |

EXAMPLE 4

|  |  |  |
| --- | --- | --- |
| Polyacrylamide | 30% | 30-50% |
| Glycerol | 70% | 50-70% |

EXAMPLE 5

|  |  |  |
| --- | --- | --- |
| Polyacrylamide | 21.5% | 2-25% |
| Polyacrylic acid | 12.5% | 2-25% |
| Glycerol | 50% | 40-70% |
| Vinyl acetate-dioctyl maleate | 16% | 10-25% |

EXAMPLE 6

|  |  |  |
| --- | --- | --- |
| Polacrylamide | 37% | 20-40% |
| Glycerol | 57% | 50-70% |

| -continued | | |
| --- | --- | --- |
| Water | 6% | 1-25% |

What is claimed is:

1. A flexible, liquid-absorbent, adhesive bandage to be applied to a patient comprising:
a flexible backing element selected from the group comprised of cotton, paper, synthetic fabric or plastic,
a substrate attached to said backing element comprising a homogeneous, hydrophilic, stable matrix having adhesive properties for adhesion to the skin and being sufficiently pliant to conform to the shape of the body contours, said matrix including a solid phase comprising about 30% to 50% of the total weight of the matrix and including a synthetic resin selected from the group comprising polyacrylic acid, polyacrylamide and their cogeners, and a liquid phase consisting of a solution or emulsion of carbohydrate and/or protein and comprising from about 40% to 70% by weight of the matrix, said matrix having been sterilized by irradiation, whereby the matrix is capable of effectively absorbing liquid exudate from a wound to which it is applied and being capable of remaining dimensionally stable and tacky during such absorption.

2. The bandage as defined in claim 1 wherein said liquid phase comprises a solution of a polysaccharide.

3. The bandage as defined in claim 1 wherein said liquid phase comprises a hydric alcohol such as glycerol.

4. The bandage as defined in claim 1 wherein the solid phase of matrix includes a natural gum selected from the group comprising karaya gum, gum acacia, locust bean gum and guar gum.

5. The bandage as defined in claim 4 wherein said liquid phase comprises a glycerol.

6. The bandage as defined in claim 4 wherein said matrix is comprised of 10% to 40% by weight of karaya, 2% to 20% by weight of polyacrylamide, and 40% to 70% by weight of glycerol.

7. The bandage as defined in claim 1 wherein said matrix is comprised of 30% to 50% by weight of polyacrylamide and 50% to 70% by weight of glycerol.

8. The bandage as defined in claim 1 wherein said matrix if formed 2% to 25% by weight of polyacrylamide and 2% to 25% by weight of polyacrylic acid, and 40% to 70% by weight of glycerol.

9. The bandage as defined in claim 1 wherein said matrix if formed of 30% to 50% by weight of polyacrylic acid and 50% to 70% by weight of glycerol.

* * * * *